(12) United States Patent
Miljkovic et al.

(10) Patent No.: US 8,088,752 B2
(45) Date of Patent: Jan. 3, 2012

(54) METHODS FOR METABOLIC MODULATION

(75) Inventors: Dusan Miljkovic, San Diego, CA (US);
Jovan Hranisavljevic, Belgrade (RS);
Zbigniew Pietrzkowski, Dyer, IN (US)

(73) Assignee: VDF FutureCeuticals, Inc., Momence, IL (US)

( * ) Notice: Subject to any disclaimer, the term of this patent is extended or adjusted under 35 U.S.C. 154(b) by 336 days.

(21) Appl. No.: 12/419,950

(22) Filed: Apr. 7, 2009

(65) Prior Publication Data
US 2009/0203638 A1    Aug. 13, 2009

Related U.S. Application Data

(62) Division of application No. 10/567,875, filed as application No. PCT/US2004/025512 on Aug. 5, 2004, now abandoned.

(60) Provisional application No. 60/493,447, filed on Aug. 8, 2003, provisional application No. 60/499,637, filed on Sep. 2, 2003, provisional application No. 60/511,746, filed on Oct. 15, 2003, provisional application No. 60/562,496, filed on Apr. 14, 2004, provisional application No. 60/562,384, filed on Apr. 14, 2004.

(51) Int. Cl.
*A61K 31/70* (2006.01)

(52) U.S. Cl. .............. 514/45; 514/46; 514/866
(58) Field of Classification Search .............. 514/45, 514/46
See application file for complete search history.

(56) References Cited

U.S. PATENT DOCUMENTS

| | | | |
|---|---|---|---|
| 3,506,643 A | 4/1970 | Thiel et al. | |
| 3,851,056 A * | 11/1974 | Stork et al. | 514/46 |
| 5,688,774 A | 11/1997 | Jacobson et al. | |
| 6,294,522 B1 * | 9/2001 | Zablocki et al. | 514/46 |

FOREIGN PATENT DOCUMENTS

| | | |
|---|---|---|
| WO | 03/88921 | 10/2003 |
| WO | 03/97662 | 11/2003 |

* cited by examiner

*Primary Examiner* — Kevin E Weddington
(74) *Attorney, Agent, or Firm* — Fish Associates, PC

(57) ABSTRACT

Pharmaceutical compositions include compounds with cytokinin activity to modulate glucose and/or lipid metabolism in a mammal. Especially preferred compounds include those comprising a purine scaffold, and it is further preferred that contemplated compositions are employed to prevent and/or treat various diseases, including pre-diabetes, insulin resistance, type-2 diabetes, Syndrome X, and dyslipidemia. In still further preferred aspects, compounds with cytokinin activity are used to activate AMPK and/or Akt. Consequently, various diseases associated with dysregulation of AMPK and/or Akt may be treated using the compounds of the present inventive subject matter.

14 Claims, No Drawings

METHODS FOR METABOLIC MODULATION

This application is a divisional application of our copending U.S. application with the Ser. No. 10/567,875, which was filed Jan. 10, 2007 which is a national phase of PCT application number PCT/US04/25512 filed Aug. 5, 2004 which claims the benefit of our U.S. Provisional Patent Applications with the Ser. Nos. 60/493,447, 60/499,637, 60/511,746, 60/562,384, and 60/562,496, which were filed Aug. 8, 2003, Sep. 2, 2003, Oct. 15, 2003, Apr. 14, 2004, and Apr. 14, 2004, respectively, all of which are incorporated by reference herein.

FIELD OF THE INVENTION

The field of the invention is pharmaceutical compositions and methods for metabolic modulation.

BACKGROUND OF THE INVENTION

Pre-diabetes, insulin resistance, type-2 diabetes (non-insulin dependent diabetes, NIDDM), syndrome X, and dyslipidemia pose a substantial health threat to a significant portion of the population in the US and other industrialized nations. For example, about 6.3% of all US citizens are diagnosed with diabetes, and another 5.2 million people are suspected to be undiagnosed (National diabetes fact sheet: General information and national estimates on diabetes in the United States, 2003. Rev ed. Atlanta, Ga.: U.S. Department of Health and Human Services, Centers for Disease Control and Prevention, 2004). Worse yet, about 40 percent of U.S. adults ages 40 to 74 currently satisfy the conditions for a positive diagnosis of pre-diabetes, which frequently progresses to type 2 diabetes within 10 years unless treated (Press release U.S. Department of Health and Human Services, Apr. 4, 2004: Revised Definition Of Pre-Diabetes).

With respect to syndrome X (defined as a constellation of metabolic abnormalities in serum or plasma insulin/glucose level ratios, lipids, uric acid levels, vascular physiology, and coagulation factor imbalances by the American Association of Clinical Endocrinologists), it is estimated that about 20% of adults in the U.S. will fall within the diagnostic criteria, with a prevalence approaching 50% in the elderly (News release: American Association for Clinical Chemistry, (2004)). Similarly, a significant fraction of the U.S. population is diagnosed with dyslipidemia. For example, approximately 29% of the U.S. population are thought to require dietary intervention for high blood cholesterol (Centers for Disease Control and Prevention in JAMA. 1993 Jun. 16; 269(23):3009-14).

Current Pharmaceutical Interventions

Various efforts are presently known to treat pre-diabetes, insulin resistance, syndrome X, and/or NIDDM. Among other compound classes, biguanides have shown relatively high therapeutic effect, and a typical representative of this class is metformin. Biguanides generally will not affect insulin secretion, and will increase peripheral glucose uptake while decreasing hepatic gluconeogenesis. Most biguanides will activate AMPK without significantly altering the AMP:ATP ratio. Unfortunately, many biguanides also produce lactic acidosis, which may become a life-threatening condition, especially where a patient has renal insufficiency. Still further, biguanide therapy is often counter-indicated where a patient takes other drugs that interfere with renal function.

Other commonly prescribed drugs to lower blood glucose include thiazolidinediones (a.k.a. glitazones), which are thought to increase insulin sensitivity by activating the PPAR gamma nuclear receptor. Thus, adipose tissue, skeletal muscle and liver tissue are typical target organs, in which glucose uptake is enhanced via overexpression of GLUT4. However, various glitazones have been withdrawn from the market or development has discontinued due to relatively high hepatotoxicity. Moreover, numerous other side effects include weight gain and fluid retention. Recently, overstimulation of PPAR gamma has also been implicated in increased chances of developing colorectal cancer.

In yet further known therapeutic approaches, sulfonyl ureas and/or meglitinides were employed to stimulate insulin production/release from the pancreas. Compounds falling in this classes of drugs are thought to act as potassium channel blockers that interact with the respective receptors in the pancreas. While such compounds have found relatively common use in the treatment of some forms of type 2 diabetes, various disadvantages remain. Among other things, sulfonyl ureas and/or meglitinides may produce hypoglycemia. Worse yet, tolbutamide (a sulfonylurea) was shown to increase the risk of cardiovascular mortality, which may also be the case in other sulfonylureas and meglitinides due to their common mode of action. Additionally, various combinations of the above drugs are known to balance a particular effect with tolerability, blood glucose control, and other clinical parameters. However, while some disadvantages may be mitigated, other disadvantages nevertheless remain.

Finally, where the pancreas fails to produce and/or release sufficient quantities of insulin, native, heterologous, and/or recombinant insulin may be administered to a patient via injection. There are numerous insulin formulations known in the art (e.g., fast acting, intermediate acting, long acting), and depending on the type of insulin, problems may arise with immunogenicity, tolerability, and/or long-term effectiveness. Furthermore, correct administration of such preparations must be verified via blood tests that add to the inconvenience of such therapy.

Non-Pharmaceutical Interventions

Numerous nutritional supplements are advertised as being indicated for patients diagnosed with syndrome X, pre-diabetes, insulin resistance, and/or NIDDM. Among other compositions, various chromium compounds and food products containing such compounds may be ingested to increase glucose utilization. However, at least some of these nutritional supplements exhibit significant toxicity (e.g., Cr-picolinate), and/or the chromium has only relatively low solubility and/or bioavailability. Alternatively, blood glucose was reported to be modulated using barley extracts as described by Miljkovic et al. in WO 02/072148, WO 01/66146, and WO 2004/021980, all of which are incorporated by reference herein. However, to achieve substantial normalizing effect, at least some forms of such products need to be ingested at rather large amounts.

There are still further numerous nutritional supplements making one or more claims related to syndrome X, pre-diabetes, insulin resistance, and/or NIDDM, and many of such compositions include various plant extracts, vitamins, amino acids, minerals, and other components thought to be involved in normalization of blood glucose. However, such claims are typically not verified or endorsed by the FDA, and the efficacy for the advertised purpose is questionable for all or almost all of these supplements.

Cytokinins

Cytokinins have been implicated in numerous aspects of growth and development in plants, and typical cytokinin-modulated processes include cell division, shoot initiation and growth, leaf senescence, and photomorphogenic development (see e.g., Mok, D. W. S., and M. C. Mok. 1994, Cytokinins: Chemistry, Activity and Function: CRC Press, Boca Raton, Fla.). Most naturally occurring cytokinins are adenine derivatives with distinct substitutions attached to the $N^6$-position of the adenine ring. Exemplary $N^6$-substituents include isoprenoid side chains, and cycloalkyl structures. For further review of structure, biological action, and other relevant properties of cytokinins, reference is made to "The Arabidopsis Book", by Joseph Kieber on pages 1-25.

Remarkably, cytokinins were also detected in human urine (Biochem Biophys Res Commun. 2000 Dec. 9; 279(1):69-73), and numerous effects of cytokinins and cytokinin ribosides are reported in the relevant literature. For example, Wyszko et al attribute anti-oxidant properties to cytokinins (Biochim Biophys Acta. 2003 Feb. 20; 1625(3):239-45). In other uses, kinetin was reported to exhibit anti-ageing and anti-tumorigenic effect (Biochem Biophys Res Commun. 1994 Jun. 15; 201(2):665-72). In yet another contemplated human use, zeatin was suggested as an anti-Alzheimer's drug due it's inhibition of acetylcholinesterase (Mol Cells. 2002 Feb. 28; 13(1): 113-7).

The patent literature provides further uses of cytokinins and related compounds for treatment of various diseases. For example, Rattan describes in U.S. Pat. No. 5,602,139 the topical use of cytokinins to achieve healthy and youthful appearance of skin, and further teaches in U.S. Pat. No. 5,614,407 the oral use of cytokinin-containing compositions to delay morphological changes associated with ageing. Izuka describes in U.S. Pat. No. 4,629,627 use of a basidiomycetes polysaccharide extract in combination with cytokinins for treatment of viral hepatitis. Oral administration of cytokinins was reported to treat inflammation and associated discomfort as described in U.S. Pat. No. 5,151,425 to LeaLand. In still further reported uses, cytokinins were employed to treat skin hyperproliferative diseases as described in U.S. Pat. Nos. 5,021,422 and 5,164,394 to Bolund et al., while Malik reports in WO 03/094907 the topical use of cytokinins in the treatment of skin wounds, wherein cytokinins are described as increasing proliferation of fibroblasts.

In yet further known uses, cytokinins were described as therapeutic agents having anticancer, mitotic, immunosuppressive, and anti-senescent effect in human, animals, and plants as published in WO 01/49688 and WO 03/040144. Contemplated treatments for auto-immune diseases included psoriasis, multiple sclerosis, type-1 diabetes, and graft-versus-host disease.

Cytokinin Glycosides

Cytokinin glycosides (typically N6-substituted adenosines) have also found use in various applications. For example, various N6-aralkyl substituted adenosines were found to have positive effect on the blood circulation of the coronary artery vasculature as described in U.S. Pat. Nos. 3,506,643 and 3,502,649 to Thiel et al. Furthermore, Storck et al. reported certain N6-substituted adenosines as having anti-lipolytic and anti-hyperlipidemic effect as described in U.S. Pat. No. 3,851,056. Similarly, Kampe et al. described in U.S. Pat. No. 3,509,129 selected N6-aralkyl substituted adenosines as coronary dilating agents. Antiviral and anti-prion use of selected cytokinin ribosides was reported in U.S. Pat. No. 5,681,831 to Pendergast. In still other uses, cytokinin glycosides were demonstrated to have therapeutic use to treat gastroesophageal reflux, delayed gastric emptying, or irritable bowel syndrome as described in U.S. Pat. No. 5,055,569 to Becker et al., and Jacobson et al. described in U.S. Pat. No. 5,688,774 various cytokinin glycosides as A3 adenosine receptor agonists.

Further Heterocyclic Compounds

Further heterocyclic compounds (e.g., substituted benzimidazoles, multi-substituted purines, etc.) were reported as having anti-viral, and antineoplastic effect, or as having anti-apoptotic effect. Exemplary compounds and uses are described in U.S. Pat. No. 6,482,843 to Quada Jr., US2003/0069259 to Borcherding et al. and U.S. Pat. No. 6,413,974 to Dumont et al.

Thus, while numerous compositions and methods for metabolic control are known in the art, all or almost all of them, suffer from one or more disadvantages. Similarly, numerous uses for cytokinins are known in the art. However, none of the known methods teaches or suggests use of cytokinins for specific metabolic modulation. Therefore, there is still a need for improved pharmaceutical compositions, and especially for pharmaceutical compositions that effect metabolic modulation.

SUMMARY OF THE INVENTION

The present invention is directed to various pharmaceutical compositions and methods of metabolic modulation, and particularly to compositions and methods in which a cytokinin is employed to modulate glucose and/or lipid metabolism.

In one aspect of the inventive subject matter, a pharmaceutical composition includes a pharmaceutically acceptable carrier in combination with a compound having cytokinin activity in a dosage form effective to modulate glucose metabolism in a mammal when the composition is administered to the mammal at a concentration effective to modulate glucose metabolism.

Particularly preferred compounds with cytokinin activity will comprise a purine or pyrimidine scaffold and may have a structure according to Formulae I, II, or III:

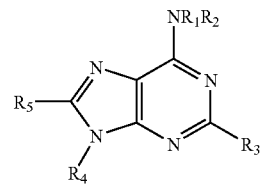

Formula I

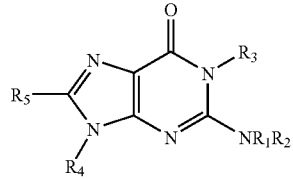

Formula II

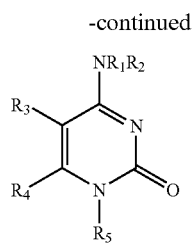

Formula III in which $R_1$ and $R_2$ are independently H, optionally substituted alkyl, optionally substituted alkenyl, optionally substituted alkynyl, optionally substituted aryl, optionally substituted alkaryl, optionally substituted heteroaryl, optionally substituted heteroalkaryl, optionally substituted heterocycle, OH, NOH, CN, $NR_3R_4$, NHCOR, $NHCONH_2$, $NHCSNH_2$, $OCH_2COOH$, $OCH_2CONH_2$, $OCH_2CONHR$, $OC(CH_3)_2COOH$, $OC(CH_3)_2CONH_2$, $NHCH_2COOH$, $NHCH_2CONH_2$, $NHSO_2R$, $NHSO_2CF_3$, $OCH_2$-heterocycle, $PO_3H$, $SO_3H$, $(CH_2)_{1-3}COOH$, CH=CHCOOH, $O(CH_2)_{1-4}COOH$, $NHCOCH_2CH(OH)COOH$, $CH(COOH)_2$, $CH(PO_3H)_2$, NHCHO, $OCH_2CH_2CH_2COOH$;

R is independently $R_1$, and with the proviso that $R_1$ and $R_2$ in $NR_1R_2$ are not H at the same time; and in which $R_3$, $R_4$, and $R_5$ are independently H, optionally substituted alkyl, optionally substituted alkenyl, optionally substituted alkynyl, optionally substituted aryl, optionally substituted alkaryl, optionally substituted heteroaryl, optionally substituted heteroalkaryl, optionally substituted heterocycle, $NH_2$, OH, NOH, CN, $CF_3$, O-alkyl, S-alkyl, NH-alkyl, carbohydrate radical, carbocyclic radical, or carbohydrate analog radical.

Therefore, particularly preferred compounds with cytokinin activity include N6-benzyladenine, N6-benzyladenine hydrochloride, N6-benzyladenosine, N6-benzyladenine-3-glucoside, N6-benzyladenine-7-glucoside, N6-benzyladenine-9-glucoside, N6-benzyl-9-(2-tetrahydropyranyl)adenine, N6-benzyladenosine-5'-monophosphate, dihydrozeatin, dihydrozeatin riboside, dihydrozeatin-7-β-D-glucoside, dihydrozeatin-9-β-D-glucoside, dihydrozeatin-O-glucoside, dihydrozeatin-O-glucoside riboside, dihydrozeatin riboside-5'-monophosphate, dihydrozeatin-O-acetyl, N6-isopentenyladenine, N6-isopentenyladenosine, N6-isopentenyladenosine-5'-monophosphate, N6-isopentenyladenine-7-glucoside, N6-isopentenyladenine-9-glucoside, 2-methylthio-N-6-isopentenyladenosine, 2-methylthio-N-6-isopentenyladenine, 2-thio-N-6-isopentenyladenine, 2-benzylthio-N-6-isopentenyladenine, kinetin, kinetin riboside, kinetin-9-glucoside, kinetin riboside-5'-monophosphate, meta-topolin, meta-topolin riboside, meta-topolin-9-glucoside, ortho-topolin, ortho-topolin riboside, ortho-topolin-9-glucoside, trans-zeatin, trans-zeatin riboside, cis-zeatin, cis-zeatin riboside, trans-zeatin-7-glucoside, trans-zeatin-9-glucoside, trans-zeatin-O-glucoside, trans-zeatin-O-glucoside riboside, trans-zeatin riboside-5'-monophosphate, trans-zeatin-O-acetyl, 2-chloro-trans-zeatin, N2-acyl-guanine, N2-acyl-guanosine, 2-methylthio-trans-zeatin, and 2-methylthio-trans-zeatin riboside, each of which may be present as a salt, a hydrate, in form of a prodrug, or as a metabolite.

Furthermore, it should be noted that contemplated pharmaceutical compositions may additionally include a second pharmaceutical agent, and most preferably a pharmaceutical agent for treatment of syndrome X, pre-diabetes, insulin resistance, type-2 diabetes, and dyslipidemia. Thus, suitable second pharmaceutical agents include various biguanides, sulfonyl ureas, meglitinides, thiazolidinediones, and additional compounds having cytokinin activity.

Therefore, in another aspect of the inventive subject matter, a method of modulating glucose metabolism in a mammal includes a step of administering contemplated compounds at a dosage effective to modulate glucose metabolism in the mammal, wherein the mammal is preferably diagnosed with at least one of syndrome X, pre-diabetes, insulin resistance, type-2 diabetes, and dyslipidemia. Alternatively, administration of contemplated compositions may also be prophylactically to prevent syndrome X, pre-diabetes, insulin resistance, type-2 diabetes, and/or dyslipidemia. While not wishing to be bound by any specific theory or hypothesis, the inventors contemplate that the compounds according to the inventive subject matter will modulate the glucose metabolism by increasing glucose uptake in a muscle cell, and/or decreasing gluconeogenesis in a hepatocyte.

In a still further aspect of the inventive subject matter, the inventors contemplate a method of modulating lipid metabolism in a mammal (e.g., Syndrome X and dyslipidemia), wherein the methods includes a step of administering a compound according to claim 1 at a dosage effective to modulate glucose metabolism in the mammal, wherein the compound is not a N6-aralkyladenosine. Particularly contemplated modulation of lipid metabolism includes decreasing total serum cholesterol, LDL-cholesterol, and/or triglycerides.

In yet another aspect of the inventive subject matter, the inventors contemplate a method of treating a condition in a mammal associated with dysregulation of at least one of AMPK and Akt, wherein the method comprises a step of administering one or more of contemplated compounds at a dosage effective to activate at least one of AMPK and Akt. Among other diseases, conditions associated with AMPK/Akt dysregulation include cardiovascular diseases, type 2 diabetes, and neoplastic diseases.

Additionally, the inventors contemplate that the concentration of compounds with cytokinin activity in a biological fluid of a mammal is correlated with the likelihood to develop, or presence of a metabolic disorder (e.g., pre-diabetes, insulin resistance, type-2 diabetes, syndrome X, and dyslipidemia). Therefore, a test may include determination of contemplated compounds, and association of the concentration with the likelihood to develop, or presence of a metabolic disorder.

Various objects, features, aspects and advantages of the present invention will become more apparent from the following detailed description of preferred embodiments of the invention.

DETAILED DESCRIPTION

The inventors have unexpectedly discovered that numerous cytokinins and cytokinin glycosides have various desirable biological properties in mammals that heretofore have not been recognized.

More specifically, and in one aspect of the inventive subject matter, contemplated compositions and methods have been proven effective to treat at least one of pre-diabetes, insulin resistance, type-2 diabetes, syndrome X, and dyslipidemia in human. While not limiting to the inventive subject matter, the inventors contemplate that such effects may be due to activation of GLUT4, AMPK, and/or Akt, and reduction in activity of ACC and/or HMGCoA reductase.

Definition Of Terms

The term "cytokinin" as used herein refers to a variety of compounds with biological activity, and especially cytokinin activity. Particularly contemplated cytokinins include those having a purine scaffold, and even more preferably those having an N6-substituted adenine scaffold. However, it should be recognized that the term cytokinin also includes various compounds with a scaffold other than a purine scaffold (e.g., pyrimidine scaffold), and specifically contemplated cytokinins are addressed below. It should be noted that metformin, AICA (4-Amino-5-imidazolecarboxamide), and AICAR (4-Amino-5-imidazolecarboxamide riboside) are expressly excluded from the definition of the term "cytokinin" and compound with "cytokinin activity". Among various other biological activities, cytokinins may be described as compounds having modulatory effect on plant cell growth and differentiation. However, and in the context of the present inventive subject matter, it should be recognized that cytokinins also have biological activity in mammalian systems, and especially human. Remarkably, cytokinins were shown to have substantial effect on glucose import and utilization in various tissues, as well as marked effect in modulation of kinase activities, and lipid profiles in vivo.

The term "cytokinin glycoside" as used herein refers to either a naturally occurring cytokinin or a synthetic cytokinin, wherein the naturally occurring cytokinin or synthetic cytokinin is covalently coupled to a carbohydrate group (or carbohydrate analog). Typically, such covalent coupling will be a glycosidic bond, and most typically with a ribose. However, other carbohydrate groups are also contemplated. For example, alternative carbohydrate groups include arabinose, erythrose, carbohydrate oligomers and polymers, and especially glucans. Further suitable carbohydrate analogs include carbocyclic compounds, non-cyclic carbohydrates, and heterocyclic compounds. Thus, the covalent bond may also be a non-glycosidic bond, and may even include a spacer having one to several carbon/non-carbon atoms that connect the cytokinin with the carbohydrate group (or carbohydrate analog). With respect to the biological effects of cytokinin glycosides, it should be noted that in some cases a biological effect is reduced or even abolished, while in other cases the biological effect is changed and/or maintained.

Unless expressly stated to the contrary, the terms "cytokinin" and cytokinin glycoside" also refer to mixtures of chemically distinct cytokinins and cytokinin glycosides, respectively. It should further be recognized that all isomeric forms of contemplated cytokinins (and mixtures thereof) are contemplated and considered suitable for use herein. Exemplary isomeric forms include stereoisomers, enantiomers, tautomers, optical isomers, etc.). Still further, there are numerous chemical modifications that can be made to convert a cytokinin to a modified cytokinin (which may or may not abolish the desired effect), and exemplary modifications include esterification, amidation, oligomerization, and other covalent additions, all of which are contemplated herein. Similarly, it should be recognized that where it is a metabolite of the cytokinin that exhibits the desired activity (or where the cytokinin is the metabolite), such metabolites are also contemplated.

As further used herein, the term "isolated cytokinin" refers to a cytokinin having a purity of at least 70%, wherein such cytokinin may be isolated from a natural source or isolated/obtained from a synthetic procedure. As still further used herein, the term "naturally occurring cytokinin" refers to a cytokinin isolated from a plant, algae, or microorganism. In contrast, the term "synthetic cytokinin" as used herein refers to a cytokinin that is isolated and/or obtained from a synthetic procedure, wherein the structure of the synthetic cytokinin may be identical with the structure of the naturally occurring cytokinin.

The term "cytokinin activity" as used herein refers to an activity that is characterized as a positive test result in at least one of the following test protocols:

(1) Soy bean callus culture: A positive test result is obtained when a test compound leads to an increase of at least 10% (and more typically at least 20%) in dry weight of the callus or at least 30% (and more typically at least 45%) in fresh weight of the callus as compared to a control without cytokinin in the callus growth medium. A general procedure is provided in U.S. Pat. No. 4,995,903 (Example 3).

(2) Cucumber cotyledon test: A positive test result is obtained when a test compound has an $ED_{50}$ of less than 200. The test procedure is a modification of the protocol described in Plant Physiology (1982), 69: 695 et seq., and general procedure for the cucumber cotyledon test is provided in U.S. Pat. No. 4,995,903 (Example 2).

(3) Tobacco callus test: A positive test result is obtained when a test compound leads to an increase of at least 10% (and more typically at least 20%) in fresh weight of the callus as compared to a control. A general procedure is provided in *Journal of Biological Chemistry* (1975), 250(18): 7343-7351.

(4) Cytokinin response regulator test: A positive test is obtained when a test compounds increases at least four of six type-A response regulators in an amount of at least 10% in a test system as described by Asakura et al. in *Plant Mol Biol.* 2003 May; 52(2):331-341, which is incorporated by reference herein.

(5) Alternatively, it is also contemplated that cytokinin activity may be identified by virtue of activation of AMPK, and a quantitative assay is described in *Biochem. Biophys. Res. Commun.* (1994), 200(3):1551-6 by Sullivan et al. (Characterization of 5'-AMP-activated protein kinase in human liver using specific peptide substrates and the effects of 5'-AMP analogues on enzyme activity). A positive test result is obtained when a test compound increases phosphorylation of a substrate at least 5% over control.

Cytokinin activity of a compound may also be identified by its ability to increase yeast fermentation in an assay as previously described. Typically, cytokinin activity is monitored by quantification of brewers' yeast fermentation rate under anaerobic conditions using a modified Warburg method (Mirsky, N. et al., J. Inorg. Biochem. 13(1):11-21 (1980), which is incorporated by reference herein):

Two grams of wet brewers yeast cells (about 20% dry weight) are suspended in fermentation medium (25 ml of 60 mM phosphate buffer, pH 5.7 and 10 ml of 5% (w/v) glucose solution), and aliquots of a cytokinin or cytokinin-containing composition are added to the fermentation medium for testing. Incubations are carried out in 50 ml fermentation flasks at 25° C. for 60 minutes. The fermentation rates are determined from the volume of $CO_2$ generated.

For further guidance, the following papers describe detection and/or measurement of cytokinin activity, all of which are incorporated by reference herein. Skoog et al. (1967) *Phytochem.* 6:1169-1192; Morris (1986) *Ann. Rev. Plant Physiol.* 37:509-538; Horgan (1984) in *Advanced Plant Physiol.* pp. 53-75; and Letham and Palni (1983) in *Ann. Rev. Plant Physiol* 34: 163-197.

As still further used herein, the term "modulate glucose metabolism" means that at least one of glucose uptake into a cell and/or tissue is increased, that AMPK is activated, that Akt is activated, and/or that hepatic gluconeogenesis is increased or decreased. Therefore, and from a systemic perspective, the term "modulation of glucose metabolism" also refers to a normalization of glucose tolerance where abnormal glucose tolerance was previously observed, to a decrease of fasting and/or postprandial serum glucose concentration.

Thus, it should be appreciated that compounds that modulate glucose metabolism include those for treatment of pre-diabetes, type II diabetes, syndrome X (a.k.a. metabolic syndrome), and insulin resistance. However, it should be noted that the term "modulate glucose metabolism" expressly excludes treatment of type 1 diabetes.

Similarly, the term "modulate lipid metabolism" means that at least one of a serum triglyceride concentration, serum HDL-cholesterol, serum total cholesterol, and serum fatty acid concentration is reduced, which may be concurrent with a reduction in 3-Hydroxy-3-methyl glutaryl CoA (HMG-COA) reductase expression and/or activity, and/or reduction in acetyl coA carboxylase (ACC) activity (which may be concurrent with an increase in beta oxidation in selected tissues). Therefore, compounds that modulate lipid metabolism include those for treatment of dyslipidemia.

The term "alkyl" as used herein refers to unsaturated hydrocarbon groups in a straight, branched, or cyclic configuration (also referred to as cycloalkyl, see below), and particularly contemplated alkyl groups include lower alkyl groups (i.e., those having six or less carbon atoms). Exemplary alkyl groups are methyl, ethyl, propyl, isopropyl, butyl, sec-butyl, tertiary butyl, pentyl, isopentyl, hexyl, isohexyl, etc. The term "alkenyl" as used herein refers to an alkyl as defined above and having at least one double bond. Thus, particularly contemplated alkenyl groups include straight, branched, or cyclic alkenyl groups having two to six carbon atoms (e.g., ethenyl, propenyl, butenyl, pentenyl, etc.). Similarly, the term "alkynyl" as used herein refers to an alkyl or alkenyl as defined above and having at least one triple bond. Especially contemplated alkynyls include straight, branched, or cyclic alkynes having two to six total carbon atoms (e.g., ethynyl, propynyl, butynyl, pentynyl, etc.).

The term "cycloalkyl" as used herein refers to a cyclic alkane (i.e., in which a chain of carbon atoms of a hydrocarbon forms a ring), preferably including three to eight carbon atoms. Thus, exemplary cycloalkanes include cyclopropyl, cyclobutyl, cyclopentyl, cyclohexyl, cycloheptyl, and cyclooctyl. It should further be appreciated that cycloalkyls may also include a double or triple bond (and may therefore also be termed cycloalkenyl or cycloalkynyl). The term "aryl" as used herein refers to an aromatic carbon atom-containing ring, which may further include one or more non-carbon atoms (then also referred to as heteroaryl). Thus, contemplated aryl groups include cycloalkenyls (e.g., phenyl, naphthyl, etc.) and pyridyl. Further contemplated aryl groups may be fused (i.e., covalently bound) to another aryl group, and are thus termed "fused aryl".

As also used herein, the terms "heterocycle", "cycloheteroalkyl", and "heterocyclic base" are used interchangeably herein and refer to any compound in which a plurality of atoms form a ring via a plurality of covalent bonds, wherein the ring includes at least one atom other than a carbon atom. Particularly contemplated heterocyclic bases include 5- and 6-membered rings with nitrogen, sulfur, or oxygen as the non-carbon atom (e.g., imidazole, pyrrole, triazole, dihydropyrimidine, indole, pyridine, thiazole, tetrazole etc.). Further contemplated heterocycles may be fused (i.e., covalently bound) to another ring or heterocycle, and are thus termed "fused heterocycle" or "fused heterocyclic base" as used herein.

The term "alkoxy" as used herein refers to straight or branched chain alkoxides, wherein the hydrocarbon portion may have any number of carbon atoms (and may further include a double or triple bond). For example, suitable alkoxy groups include methoxy, ethoxy, isopropoxy, etc. Similarly, the term "alkylthio" refers to straight or branched chain alkyl-sulfides, wherein the hydrocarbon portion may have any number of carbon atoms (and may further include a double or triple bond). For example, contemplated alkylthio groups include methylthio (MeS—), ethylthio, isopropylthio, etc. Likewise, the term "alkylamino" refers to straight or branched alkylamines, wherein the hydrocarbon portion may have any number of carbon atoms (and may further include a double or triple bond). Furthermore, the N-hydrogen of the alkylamino group may be substituted with another alkyl group. Therefore, exemplary alkylamino groups include methylamino, dimethylamino, ethylamino, diethylamino, isopropylamino, t-butylamino, etc.

The term "halogen" as used herein refers to fluorine, chlorine, bromine, and iodine.

It should also be recognized that all, or almost all of the above-defined groups may be substituted with one or more substituents, which may in turn be substituted as well. For example, where a hydrogen atom in an alkyl is substituted with an amino group, one or both hydrogen atoms in the amino group may be substituted with another group (e.g., alkyl or alkenyl).

The term "substituted" as used herein refers to a replacement of an atom or one functional group (e.g., H, $NH_2$, or OH) with another atom or functional group, and particularly contemplated functional groups include nucleophilic groups (e.g., $—NH_2$, —OH, —SH, —NC, etc.), electrophilic groups (e.g., C(O)OR, C(X) OH, etc.), polar groups (e.g., —OH), non-polar groups (e.g., aryl, alkyl, alkenyl, alkynyl, etc.), ionic groups (e.g., $—NH_3^+$), and halogens (e.g., —F, —Cl). Further contemplated functional groups include NHCOR, $NHCONH_2$, $NHCSNH_2$, $OCH_2COOH$, $OCH_2CONH_2$, $OCH_2CONHR$, $OC(Me)_2COOH$, $OC(Me)_2CONH_2$, $NHCH_2COOH$, $NHCH_2CONH_2$, $NHSO_2R$, $NHSO_2CF_3$, $OCH_2$-heterocycles, $PO_3H$, $SO_3H$, $(CH_2)_{1-3}COOH$, CH=CHCOOH, $O(CH_2)_{1-4}COOH$, $NHCOCH_2CH(OH)$ COOH, $CH(COOH)_2$, $CH(PO_3H)_2$, $OCH_2CH_2CH_2COOH$, NHCHO, with R being an alkyl, halogen, or H. Moreover, the term "substituted" also includes multiple degrees of substitution, and where multiple substituents are disclosed or claimed, the substituted compound can be independently substituted by one or more of the disclosed or claimed substituent moieties.

Thus, the term "functional group" and "substituent" are used interchangeably herein and refer to groups including nucleophilic groups (e.g., $—NH_2$, —OH, —SH, —NC, —CN etc.), electrophilic groups (e.g., C(O)OR, C(X) OH, C(Halogen)OR, etc.), polar groups (e.g., —OH), non-polar groups (e.g., aryl, alkyl, alkenyl, alkynyl, etc.), ionic groups (e.g., $—NH_3^+$), and halogens, as well as NHCOR, $NHCONH_2$, $NHCSNH_2$, $OCH_2COOH$, $OCH_2CONH_2$, $OCH_2CONHR$, $OC(Me)_2COOH$, $OC(Me)_2CONH_2$, $NHCH_2COOH$, $NHCH_2CONH_2$, $NHSO_2R$, $NHSO_2CF_3$, $OCH_2$-heterocycles, $PO_3H$, $SO_3H$, $(CH_2)_{1-3}COOH$, CH=CHCOOH, $O(CH_2)_{1-4}COOH$, $NHCOCH_2CH(OH)$ COOH, $CH(COOH)_2$, $CH(PO_3H)_2$, NHCHO, $OCH_2CH_2CH_2COOH$, etc., with R being an alkyl, halogen, or H.

As used herein, the term "AMPK" refers to adenosine 5'-monophosphate-activated protein kinase, which is described, for example by Fryer et al, in Biochem J. 2002 Apr. 1; 363(Pt 1): 167-74. The term "Akt" as used herein refers to a serine/threonine kinase that is also known as protein kinase B (PKB) or RAC-PK (See, for example, Brazil and Hemmings, Trends Biochem Sci 2001 November; 26(11):657-64).

The term "syndrome X" as used herein refers to a condition characterized by positive diagnosis of at least two of the following: Non-insulin-dependent diabetes, blood pressure above a level considered normal, insulin level above a level considered normal, dyslipidemia, and obesity. The term "prediabetes" as used herein refers to a condition characterized by a fasting blood sugar of higher than 100 mg/dL, but below 140 mg/dL. The term "insulin resistance" as used herein refers to a condition characterized by a reduced sensitivity to insulin in the whole body or individual tissues, including skeletal muscle, myocardium, adipose tissue, and liver. The term "type 2 diabetes" as used herein refers to a metabolic disorder resulting from the body's inability to make enough, or properly use, insulin, which is often manifested by a fasting blood sugar of higher than 140 mg/dL. The term "dyslipidemia" as used herein refers to a condition in which at least one of triglycerides, free fatty acids, total cholesterol, and LDL-cholesterol is at a level considered above normal.

Contemplated Compounds

It is generally contemplated that all compounds having cytokinin activity are suitable for use in conjunction with the teachings presented herein. Therefore, generally contemplated compounds will include naturally occurring and synthetic cytokinins, cytokinin analogs, and their respective glycosides. Exemplary synthetic and natural cytokinins, analogs, and their glycosides are described in more detail below.

In one group of contemplated compounds, suitable cytokinins, cytokinin glycosides, and cytokinin analogs will have a structure as disclosed in our co-pending provisional patent application with the Ser. No. 60/493,447, filed Aug. 8, 2003, which is incorporated by reference herein. Alternatively, or additionally, suitable further contemplated cytokinins, cytokinin glycosides, and cytokinin analogs will have a structure according to Formula (I), Formula (II), or Formula (III).

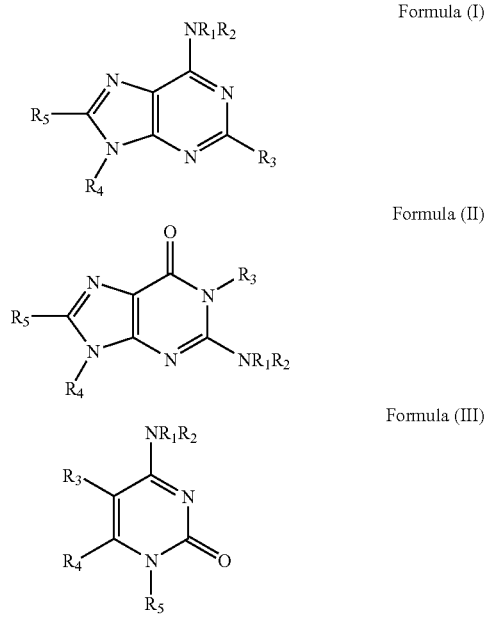

wherein $R_1$ and $R_2$ are independently H, optionally substituted alkyl, optionally substituted alkenyl, optionally substituted alkynyl, optionally substituted aryl, optionally substituted alkaryl, optionally substituted heteroaryl, optionally substituted heterocycle, OH, NOH, CN, $NR_3R_4$, NHCOR, $NHCONH_2$, $NHCSNH_2$, $OCH_2COOH$, $OCH_2CONH_2$, $OCH_2CONHR$, $OC(Me)_2COOH$, $OC(Me)_2CONH_2$, $NHCH_2COOH$, $NHCH_2CONH_2$, $NHSO_2R$, $NHSO_2CF_3$, $OCH_2$-heterocycles, $PO_3H$, $SO_3H$, $(CH_2)_{1-3}COOH$, CH=CHCOOH, $O(CH_2)_{1-4}COOH$, $NHCOCH_2CH(OH)COOH$, $CH(COOH)_2$, $CH(PO_3H)_2$, NHCHO, $OCH_2CH_2CH_2COOH$, in which R is $R_3$, and wherein $R_3$, $R_4$, and $R_5$ are independently H, optionally substituted alkyl, optionally substituted alkenyl, optionally substituted alkynyl, optionally substituted aryl, optionally substituted alkaryl, optionally substituted heteroaryl, optionally substituted heterocycle, $NH_2$, OH, NOH, CN, $CF_3$, O-alkyl, S-alkyl, NH-alkyl, carbohydrate radical (more preferably monosaccharide radical, and most preferably furanosyl), carbocyclic radical, or carbohydrate analog radical. Alternatively, or additionally numerous suitable substituted purines are described in Phytochemistry 10(1), 23-8, 1971; and ibid, 7(11), 1989-94, 1968.

Still further especially contemplated purine-type cytokinin analogs include $N^6$-alkoximinoalkyl substituted purine compounds, and exemplary compounds having cytokinin activity and their synthesis are described in U.S. Pat. No. 5,211,738 to Sasaki et al, which is incorporated by reference herein. Alternatively, the $N^6$-substituent may also include a N-mono- or N-disubstituted group, and exemplary compounds with cytokinin activity and their synthesis are described in U.S. Pat. No. 5,244,487 to Oritani et al., which is also incorporated by reference herein. Where the purine substituent in the 6-position should be relatively large (and optionally distal to the heterocyclic base via a linker), adamantly or diamantyl-6-substituted purines may be employed. Various such compounds with cytokinin activity and their synthesis are described in U.S. Pat. No. 4,751,292 to Fox, which is also incorporated by reference herein. Of course it should be recognized that the purine scaffold of the exemplary compounds listed above may further be substituted as in Formula (I) above. Further contemplated purine-type compounds with cytokinin activity include those described in U.S. Pat. No. 2,903,455, which is incorporated by reference herein.

In further contemplated aspects of the inventive subject matter, the inventors generally contemplate that one or more of the heteroatoms in the purine scaffold may be replaced by another heteroatom (most typically S, Se, or O), or a substituted carbon atom, wherein the substituent is defined as $R_3$ in Formula (I) above. Furthermore, the purine scaffold may be modified such that the five-membered ring is replaced a six-membered ring (preferably with a double bond, and most preferably with at least two conjugated double bonds). Suitable six-membered rings may include one or more heteroatoms (e.g., N, S, and/or O), and additional substituents, including those listed above as $R_3$ in Formula (I). Thus, exemplary suitable compounds with cytokinin activity will include, for example, various pyrido[3,4-d]pyrimidine derivatives, and exemplary compounds with cytokinin activity and their synthesis are described in Agri. Biol. Chem. (1986), 50: 495-97, which is incorporated by reference herein. Further contemplated heterocyclic non-purine compounds with cytokinin activity are described in U.S. Pat. No. 5,350,749 to Hackler et al., and Nishikawa, S. et al., Preparation and Structure-Activity Relationships of 4-Substituted Amino-2-methylpyrido[3,4-d]pyrimidines as Cytokinin Analogs, J. Agric. Food Chem. vol. 43, pp. 1034-1038 (1995), both of which are incorporated by reference herein.

Particularly preferred compounds include N6-benzyladenine, N6-benzyladenine hydrochloride, N6-benzyladenosine, N6-benzyladenine-3-glucoside, N6-benzyladenine-7-glucoside, N6-benzyladenine-9-glucoside, N6-benzyl-9-(2-tetrahydropyranyl)adenine, N6-benzyladenosine-5'-monophosphate, dihydrozeatin, dihydrozeatin riboside, dihydrozeatin-7-β-D-glucoside, dihydrozeatin-9-β-D-glucoside, dihydrozeatin-O-glucoside, dihydrozeatin-O-glucoside riboside, dihydrozeatin riboside-5'-monophosphate, dihydrozeatin-O-acetyl, N6-isopentenyladenine, N6-isopentenyladenosine, N6-isopentenyladenosine-5'-monophosphate, N6-isopentenyladenine-7-glucoside, N6-isopentenyladenine-9-glucoside, 2-methylthio-N-6-isopentenyladenosine, 2-methylthio-N-6-isopentenyladenine, 2-thio-N-6-isopentenyladenine, 2-benzylthio-N-6-isopentenyladenine, kinetin, kinetin riboside, kinetin-9-glucoside, kinetin riboside-5'-monophosphate, meta-topolin, meta-topolin riboside, meta-topolin-9-glucoside, ortho-topolin, ortho-topolin riboside, ortho-topolin-9-glucoside, trans-zeatin, trans-zeatin riboside, cis-zeatin, cis-zeatin riboside, trans-zeatin-7-glucoside, trans-zeatin-9-glucoside, trans-zeatin-O-glucoside, trans-zeatin-O-glucoside riboside, trans-zeatin riboside-5'-monophosphate, trans-zeatin-O-acetyl, 2-chloro-trans-zeatin, N2-acyl-guanine, N2-acyl-guanosine, 2-methylthio-trans-zeatin, and 2-methylthio-trans-zeatin riboside, each of which may further be acylated (e.g., acetylated) or heteroacylated, and/or present in form of a pharmaceutically acceptable salt.

In another group of contemplated compounds, it should be appreciated that suitable cytokinins and cytokinin analogs need not be limited to compounds having a purine scaffold or a purine analogous scaffold as exemplarily described above. Numerous compounds with cytokinin activity are known in the art that include a substituted urea or thiourea scaffold, and all of such compounds are contemplated suitable for use in conjunction with the teachings presented herein.

For example, 1-morpholino-3-phenylurea has been shown to have cytokinin activity in a cellular assay Bruce, Proc. Roy. Soc (London) Ser. B 165 (1966) 245-265. In another example, numerous substituted pyridyl(thio)ureas (e.g., N-(2-substituted-4-pyridylureas)) have been demonstrated to have cytokinin activity as described in U.S. Pat. No. 4,279,639, to Okamoto et al., which is incorporated by reference herein. Various substituted phenyl pyridinyl ureas have been described. For example, Bruce M I, Zwar J A, Proc Roy Soc (London), Sec. B. 165 (999), 1966, 245-65 disclose many N-mono- and N,N'-disubstituted ureas having cytokinin activity. N-(3,4-dichlorophenyl)-N'-3- and 4-pyridinyl ureas show such activity whereas the corresponding 2,5-dichloro compounds were inactive. In general, the authors concluded that phenyl ring substitution enhanced activity with meta substituents providing highest activity and ortho substituents lowest activity.

Similarly, various substituted pyridazine ureas and thioureas have been reported to have cytokinin activity, and exemplary compounds with such activity and their synthesis is described in U.S. Pat. No. 4,331,807, to Okamoto et al., which is incorporated by reference herein. Yet further urea-type cytokinins suitable for use in conjunction with the teachings presented herein include multi-substituted pyridinyl-phenyl ureas and thioureas (e.g., N-(2,6-disubstituted 4-pyridyl)-N'-phenylurea) as described by Isogai et al. in U.S. Pat. No. 4,308,054, which is incorporated by reference herein.

Alternatively, one or both of the (hetero)aryl and/or heterocyclic substituents of the nitrogen in the urea or thiourea may be replaced by one or more iminoamine groups to form an oligo(iminoamine) with significant cytokinin activity. Exemplary oligo(iminoamine) compounds and their cytokinin activity and synthesis are described in U.S. Pat. No. 4,571,434 to Hashizume et al, which is incorporated by reference herein. On the other hand, where it is desirable to replace the oxygen or sulfur of a urea or thiourea with a nitrogen or substituted nitrogen, substituted guanidines with cytokinin activity may be obtained. For example, particularly active guanidine compounds (e.g., alkyl, alkenyl, and/or alkynyl-substituted nitroguanidines) may be prepared as described in U.S. Pat. No. 4,995,903 to Lutz et al., which is incorporated by reference herein. See also: Rodaway, "Substituted nitroguanidines provide cytokinin activity during in vitro cultivation of plant tissues," Plant Cell Reports, 12:273-277 (1993), which is incorporated by reference herein.

In yet another group of contemplated compounds, substituted sulfonamides (e.g., O-sulfamylalkylbenzenesulfonamides) may be employed in conjunction with the teachings presented herein, and especially preferred sulfonamide compounds include those described by Sauers in U.S. Pat. No. 4,397,679, which is incorporated by reference herein. Further contemplated compounds also include various substituted ethanolamines with cytokinin activity, and especially those that include at least one aromatic group coupled to the amino group. For example, suitable N-dialkyl-alkaryl-substituted ethanolamines are described in U.S. Pat. No. 4,929,267 to Suzuki et al., which is incorporated by reference herein.

Thus, and viewed from another perspective, suitable non-purine compounds with cytokinin activity may have a general structure according to Formula (IV)

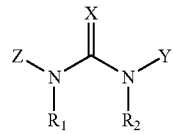

Formula (IV)

in which X is O, S, or $NR_3$, Y and Z are independently H, a polar group, optionally substituted alkyl, optionally substituted alkenyl, optionally substituted alkynyl, optionally substituted aryl, optionally substituted alkaryl, optionally substituted heteroaryl, optionally substituted heterocycle, $R_1$ and $R_2$ are independently H, optionally substituted alkyl, optionally substituted alkenyl, optionally substituted alkynyl, optionally substituted aryl, optionally substituted alkaryl, optionally substituted heteroaryl, optionally substituted heterocycle, OH, NOH, CN, or $NR_3R_4$, and wherein $R_3$ and $R_4$ are independently H, optionally substituted alkyl, optionally substituted alkenyl, optionally substituted alkynyl, optionally substituted aryl, optionally substituted alkaryl, optionally substituted heteroaryl, optionally substituted heterocycle, $NH_2$, OH, NOH, CN, $CF_3$, O-alkyl, S-alkyl, or NH-alkyl.

In a yet further contemplated group of suitable compounds, non-homogenous preparations of mycelia of and growth medium for various basidiomycetes have shown significant cytokinin activity, and exemplary preparations and activities are described in U.S. Pat. No. 4,281,021 to Iizuka et al., which is incorporated by reference herein.

Remarkably, various heterocyclic compounds have also demonstrated anti-cytokinin effect, which may be viewed as a suppression of cytokinin activity. Exemplary anti-cytokinins are described in U.S. Pat. No. 3,988,338 to Skoog et al., which is incorporated by reference herein. Additional anti-cytokinins may be readily identified following the test procedures provided above, and all known anti-cytokinins are expressly contemplated for use herein.

It should further be recognized that contemplated compounds may be present in various forms, including stereoisomeric forms (e.g., diastereomers, enantiomers), tautomeric forms (e.g., keto-enol tautomers), and may exhibit optical activity (e.g., (+) or (−) rotation), or may be present as salts, hydrates, oligomers, polymers, prodrugs, or metabolites, all of which are expressly contemplated herein. Contemplated compounds may further be present as isolated compounds, as mixtures of pure compounds, and/or as mixtures of a pure compound with an isolate. Where contemplated compounds are prepared as a prodrug, it is generally preferred that the prodrug has increased bioavailability to a target cell. For example, where it is desired that the compound is preferentially delivered to a hepatocyte, liver-targeting prodrug forms may be employed (e.g., U.S. Pat. No. 6,752,981 to Erion et al.).

Further contemplated prodrugs for contemplated compounds include those having modifications as described in, for example, Fleisher et al., Advanced Drug Delivery Reviews 19 (1996) 115-130; Design of Prodrugs, H. Bundgaard, Ed., Elsevier, 1985; H. Bundgaard, Drugs of the Future 16 (1991) 443; Saulnier et al., Bioorg. Med. Chem. Lett. 4 (1994) 1985; Safadi et al., Pharmaceutical Res. 10 (1993) 1350. Especially contemplated prodrugs include ester prodrugs of acid groups, and acyl prodrugs and carbamate prodrugs of acylatable nitrogen-containing groups (e.g., amino group, amidino group or guanidino group). For example, in the acyl prodrug or carbamate prodrug, a hydrogen atom on a nitrogen atom is replaced by an acyl group or carbamate group. These prodrugs can be prepared by customary methods familiar to those skilled in the art for the preparation of acylamines and carbamates.

Synthesis and/or isolation of contemplated compounds is well known in the art, and exemplary isolation protocols are provided, for example, in *J. Plant Res.* 2003 June; 116(3): 265-9, J. Chromatogr. A. 2002 Mar. 15; 950(1-2):21-9, or Anal. Biochem. 1989 December; 183(2):312-9. In one particularly preferred aspect of the inventive subject matter, the cytokinin or related compound is prepared from a plant or fungus, and particularly preferred plants include various grains (e.g., barley, wheat, oat, etc), various algae (e.g., laminaria), various dicots (e.g., soy), and preferred fungi particularly include shiitake (edodes spec.) mushrooms. It should also be recognized that contemplated compounds may be present in a form having reduced or even no cytokinin activity. For example, the cytokinin may be covalently bound to a glycoside or polysaccharide. In such cases, it is generally preferred that the polysaccharide preparation (e.g., a beta glucan product) is enriched in the cytokinin such that the cytokinin is present in an amount of at least 0.005 wt %, more typically at least 0.05 wt %, even more typically at least at least 0.5 wt %, and most typically at least 5 wt % of the total weight of the polysaccharide.

Similarly, exemplary synthetic protocols for cytokinins are well known in the patent literature, and reference is made to the cytokinin and cytokinin glycoside related patents listed above. Moreover, synthesis of combinatorial libraries of substituted heterocyclic bases (and especially of purine and pyrimidine-containing bases and nucleosides comprising such bases) applicable to synthesis of contemplated compounds is described in WO 03/051896, WO 03/051881, WO 03/051899, and WO 03/051897, all of which are incorporated by reference herein to the extent that they teach synthesis of libraries of substituted heterocyclic bases applicable to synthesis of contemplated compounds.

Alternatively, it is also contemplated that the compounds presented herein may be prepared as an extract from a natural source (e.g., plant seed, algae, fungus, etc.) and will therefore be less pure. For example, where contemplated compounds are isolated from a natural source, purity may be 70 wt % or less. On the other hand, where contemplated compounds are synthetically prepared, purity may be equal or greater than 70 wt %.

Contemplated Pharmaceutical Compositions

It is contemplated that pharmaceutical compositions according to the inventive subject matter comprise at least one of contemplated compounds together with a pharmaceutically acceptable carrier. Depending on the particular use, it should be recognized that formulation, route, and/or administration schedule may vary considerably, and it is generally contemplated that the specific formulation, route, and/or administration is not limiting to the inventive subject matter.

Therefore, appropriate formulations include formulations for oral, parenteral, and/or topical (including nasal, buccal, and sublingual) administration, and it is further preferred that contemplated formulations are in unit dosage form. It is still further preferred that the amount of the contemplated compound (active ingredient) that is combined with a carrier to form a unit dosage form will be the amount that produces a therapeutic effect. Thus, the percentage (% wt) of the active ingredient will typically range from about 0.01 percent to about ninety-nine percent of the total weight, more preferably from about 0.05 percent to about 90 percent, more preferably from about 0.1 percent to about 90 percent, more preferably from about 0.5 percent to about 85 percent, more preferably from about 1 percent to about 80 percent, more preferably from about 5 percent to about 70 percent, most preferably from about 10 percent to about 30 percent.

It should be appreciated, however, that the administered dose of the pharmaceutical composition will vary considerably, and a particular dose will at least in part depend on (a) the amount of active ingredient which is effective to achieve a desired therapeutic response, (b) the formulation of contemplated compounds, (c) the route of administration, (d) the pharmacokinetic and pharmacodynamic property of the particular compound, and (e) other factors, including age, sex, weight, general health, and prior medical history of the patient being treated. A person of ordinary skill in the art can readily determine and prescribe the effective amount of the pharmaceutical composition required. For example, a physician could start dosing a patient at levels lower than normally required for a desired therapeutic effect and then increase the dosage until the desired effect is achieved.

It is generally preferred that the daily dose of contemplated compounds will typically correspond to the amount of the compound which is the lowest dose effective to produce a desired therapeutic effect. Such an effective dose will generally depend upon the factors described above. Therefore, doses of the compounds according to the inventive subject matter will range from about 0.001 mg to about 100 mg per kilogram of body weight per day, more preferably from about 0.01 to about 50 mg per kg per day, and still more preferably from about 0.1 to about 40 mg per kg per day. Thus, a unit dose of contemplated compounds will range from about 0.01 mg to about 5000 mg, more preferably from about 0.01 mg to about 500 mg, still more preferably from about 0.1 mg to about 250 mg, and most preferably from about 1 mg to about 100 mg. If desired, the effective daily dose of the active compound may be administered as two, three, four, five, six or more sub-doses administered separately at appropriate intervals throughout the day, optionally, in unit dosage forms.

Viewed from another perspective, a unit dose of the contemplated compounds will preferably be an amount sufficient to increase (following oral or parenteral administration) an intracellular level of activated AMPK and/or an intracellular level of activated Akt in one or more cell types and/or tissue types of a patient, or increase GLUT4 expression and/or activity in a cell. In especially preferred embodiments, a unit dose will be selected from an amount sufficient to increase the intracellular level of activated AMPK and/or the intracellular level of activated Akt in one or more cell types and/or tissue types of said patient by at least about 20% (e.g., up to 30%, up to about 50%, up to about 75%, up to about two-fold, up to about four-fold, up to about ten-fold or up to about fifteen-fold) over pre-administration levels.

Exemplary Oral Formulations

It is generally preferred that pharmaceutical compositions according to the inventive subject matter will be orally administered, and all known forms of oral administration are deemed suitable for use herein, including solid and liquid forms. For example, solid oral forms include capsules, tablets, lozenges, powders, while preferred liquid oral forms include solutions or suspensions in suitable medium (typically aqueous solution).

Exemplary suitable pharmaceutically acceptable carriers include fillers or extenders (e.g., starch, lactose, sucrose, glucose, mannitol, and/or silicic acid), binders (e.g., alginates, gelatin, carboxymethylcellulose, or polyvinyl pyrolidone), humectants (e.g., glycerol), disintegrating agents (e.g., agar-agar, calcium carbonate, or potato or tapioca starch), solution retarding agents (e.g., paraffin), absorption accelerators (e.g., quaternary ammonium salts), wetting agents (e.g., cetyl alcohol, glycerol monostearate), absorbents (e.g., kaolin, bentonite clay), lubricants (e.g. talc, calcium stearate, magnesium stearate, solid polyethylene glycols), coloring agents, buffers, etc. Contemplated oral solid dosage may also be formulated to provide slow or controlled release of the active ingredient (e.g., using hydroxypropylmethyl cellulose in varying proportions to provide a desired release profile, other polymer matrices, liposomes and/or microspheres). It should be appreciated that preparation of contemplated oral solid dosage forms is well known in the art, and all of the known methods are deemed suitable for use in conjunction with the teachings presented herein.

Liquid dosage forms for oral administration of contemplated compounds may be prepared as pharmaceutically acceptable emulsions, micro-emulsions, solutions, suspensions, syrups and elixirs. Therefore, and depending on the particular formulation, the liquid dosage forms may also contain inert diluents, including water or other aqueous and non-aqueous solvents, solubilizing agents and emulsifiers (e.g., ethyl alcohol, isopropyl alcohol, ethyl carbonate, ethyl acetate, benzyl alcohol, etc), suspending agents (e.g., ethoxylated isostearyl alcohols, polyoxyethylene sorbitol), oils (e.g., cottonseed, corn, germ, olive, etc.), glycerol, tetrahydrofuryl alcohol, polyethylene glycols, and further known pharmaceutically acceptable liquid components.

Exemplary Topical Formulations

It should be noted that contemplated compounds may also be topically administered. Depending on the formulation and desired site of action, it is contemplated that the topical formulation may be a transdermal formulation for systemic delivery, but also as a resident formulation for local delivery. Therefore, numerous topical formulations are considered suitable for use herein, and particularly preferred formulations include ointments, creams, sprays, and gels. Where desired, contemplated compounds may be included in liposomal or transferosomal vehicles, or may be present in a dissolved or dispersed form. Typically, topical formulations will further include various excipients (e.g., animal and vegetable fats), waxes, paraffins, oils, cellulose derivatives, polyethylene glycols, silicones, bentonites, silicic acid, talc and zinc oxide, or mixtures thereof.

Exemplary Parenteral Formulations

It is generally contemplated that the compounds according to the inventive subject matter may be prepared in a formulation for parenteral use, and especially contemplated parenteral formulations will be liquid formulations for injection. Therefore, appropriate formulations will generally include a pharmaceutically acceptable solvent (e.g., sterile isotonic aqueous or non-aqueous solution), and may be prepared as a dispersion, suspension, or emulsion. Alternatively, parenteral formulations may also be provided as a kit that includes contemplated compounds and other components that may be reconstituted to a liquid product prior to use.

Examples of suitable aqueous and non-aqueous carriers which may be employed in the pharmaceutical compositions include water, ethanol, polyols (e.g., glycerol, propylene glycol, polyethylene glycol, etc.), and suitable mixtures thereof, vegetable oils, and injectable organic esters, such as ethyl oleate. Proper fluidity can be maintained, for example, by the use of coating materials, such as lecithin, by the maintenance of the required particle size in the case of dispersions, and by the use of surfactants.

In further aspects of the inventive subject matter, it should be appreciated that contemplated compositions may further comprise additional active ingredients, including compositions known to decrease a blood lipid concentration, and/or compositions known to decrease blood sugar concentrations. For example, additional active ingredients may include at least one of a vitamin and/or mineral preparation (e.g., chromium and/or vanadium, and especially chromium-containing compounds in a matrix, formulation, and/or complex as described in our co-pending provisional application with the Ser. No. 60/501,660), a biguanide (e.g. Metformin), a sulfonyl urea (e.g. Glyburide, Glimepiride), a meglitinide (e.g., Repaglandine), a thiazolidinedione (e.g. Actos, Avandia), and/or a second compound having cytokinin activity. Alternatively, it should also be appreciated that contemplated compounds may be included in a food product or nutritional supplement, and suitable food products or nutritional supplements are described in our concurrently filed International application with the title "Alimentary Compositions And Methods For Metabolic Modulation", which is incorporated by reference herein.

Contemplated Uses and Indications

Based on the inventors' findings (see examples below) and other data (not shown), it is contemplated that the compounds and pharmaceutical compositions presented herein are used as prophylactic and/or therapeutic agents for various conditions, and particularly in the prevention and/or treatment of syndrome X, pre-diabetes, insulin resistance, type 2 diabetes, and/or dyslipidemia. It should be appreciated that the term "treated" or "treatment" where used in conjunction with a medical condition refers to at least one of a resolution and/or improvement in clinical parameters of clinically abnormal values, and/or to an improvement in subjective feeling of a patient diagnosed with the condition.

Viewed from another perspective, it is also contemplated that various benefits may be derived from administration of the compounds and pharmaceutical compositions presented herein, and especially contemplated benefits relate to prevention, amelioration, and/or treatment of diseases or conditions associated with activation of AMPK, Akt, and/or activation of an AMPK/Akt-associated pathway, and the following provides exemplary guidance on contemplated benefits.

Hyperglycemia

It has recently been reported that therapeutic doses of metformin increase AMPK activity in vivo in subjects with type 2 diabetes (Diabetes, 51(7): 2074-81, 2002). Metformin treatment for 10 weeks significantly increased AMPK alpha 2 activity in the skeletal muscle, and this was associated with increased phosphorylation of AMPK on Thr172 and decreased acetyl-CoA carboxylase-2 activity. The increase in AMPK alpha 2 activity was likely due to a change in muscle energy status because ATP and phosphocreatine concentrations were lower after metformin treatment. Metformin-induced increases in AMPK activity were associated with higher rates of glucose disposal and muscle glycogen concentrations. These findings suggest that the metabolic effects of metformin in subjects with type 2 diabetes may be mediated by the activation of AMPK alpha 2. Given the hypoglycemic effect imparted by the activation of AMPK, administration of contemplated pharmaceutical products to increase AMPK activity may be useful to lower blood glucose concentrations by decreasing hepatic glucose production and increasing glucose disposal in skeletal muscle.

Reduced Insulin Sensitivity

Conditions and disorders associated with diminished insulin sensitivity of muscle glucose transport may be treated by administration of contemplated compounds. Various reports suggest that increase in insulin sensitivity of muscle glucose transport following exercise is mediated by activation of AMPK. Thus, ingestion of contemplated pharmaceutical products is thought to provide increased insulin sensitivity of muscle glucose transport.

Insulin Resistance Syndrome

Insulin resistance syndrome is associated with obesity, type 2 diabetes, and muscle paralysis (see e.g., WO 01/97816 A1 and WO 01/93874 A1). Insulin resistance syndrome is also associated with several risk factors for cardiovascular disease. In view of numerous papers suggesting that activating AMPK improves glucose tolerance, improves the lipid profile, and reduces systolic blood pressure, ingestion of contemplated pharmaceutical products to increase AMPK activity is deemed useful to reduce metabolic disturbances and/or to lower blood pressure characteristic of insulin resistance syndrome.

Insufficient Glucose Uptake in Muscle Cells

It has been observed that exercise and/or electrical stimulation of various muscles increases AMPK activity, and consequently increases glucose uptake. Based on these observations, it has been hypothesized that muscle contraction plays a role in stimulating glucose uptake in muscle, where one mechanism underlying increased uptake stems from activated AMPK increasing GLUT-4 translocation from microvesicles to sarcolemmal membranes in muscle. Based on the inventors' observation that compounds with cytokinin activity increase AMPK activity, it should be recognized that contemplated pharmaceutical products may be beneficial in enhancing glucose uptake into muscle cells (as well as being beneficial in ameliorating disorders that are characterized by decreased glucose uptake in muscle cells, or that are exacerbated by the effects of decreased glucose uptake in muscle cells).

Insulin Oversecretion

It is generally accepted in the art that activated AMPK inhibits insulin secretion, and as contemplated compounds were demonstrated to activate AMPK, it should be recognized that treatment with such compounds should provide a significant reduction in insulin secretion. Consequently, conditions associated with oversecretion of insulin may benefit from ingestion of contemplated pharmaceutical products.

Dyslipidemia

Hepatic acetyl-CoA carboxylase (ACC) and 3-hydroxy-3-methylglutaryl-CoA reductase (HMGR) are two targets for the AMPK system, catalyzing the key regulatory steps in fatty acid and sterol synthesis, respectively (Winder et al, Am J Physiol, 2777: E1-10, 1999, the entirety of which is herein incorporated by reference.) Activation of AMPK serves to inhibit both these lipid biosynthetic pathways, as well as triglyceride synthesis. Moreover, it is contemplated that activated AMPK inhibits the L-type pyruvate kinase and fatty acid synthase gene expression.

Reduction of activity of ACC in the liver cell also leads to decreases in the concentration of the product of ACC, i.e., malonyl-CoA, which has marked effects on fatty acid oxidation. Malonyl-CoA is a potent inhibitor of carnitine palmitoyltransferase-1 (CPT-1), the "gatekeeper" for entry of fatty acids into the mitochondria. In the liver, fatty acid oxidation can be considered to be an essential component of the pathway for synthesis of ketone bodies: increases in fatty acid oxidation lead to increased hepatic ketogenesis. It is therefore contemplated that administration of contemplated compounds at a concentration effective to activate AMPK in the liver would result in decreases in fatty acid, triglyceride, and sterol synthesis and increases in fatty acid oxidation and ketogenesis. Viewed from another perspective, contemplated pharmaceutical products may be useful to increase AMPK activity and thereby reduce fatty acid synthesis, sterol synthesis, triglyceride synthesis and fatty acid synthase gene expression. Of additional benefit is also the AMPK-mediated increase in activity in fatty acid oxidation and ketogenesis, where increased ketogenesis is desired.

Obesity

Hormone-sensitive lipase (HSL) is a target for AMPK in adipose tissue. Activation of AMPK has been shown to inhibit lipogenesis by phosphorylation of ACC and also to inhibit isoprenaline-stimulated lipolysis. Thus, contemplated pharmaceutical products may help reduce or even abolish lipogenesis and/or increase isoprenaline-stimulated lipolysis. Thus, and given the inhibitory role for AMPK in the process of adipose differentiation, it should be recognized that contemplated pharmaceutical products will likely inhibit adipogenesis.

Modulation of Stability of Selected mRNA Species

HuR is an RNA binding protein that functions to stabilize a variety of target mRNA transcripts, including those encoding p21, cyclinA and cyclinB1. It has been shown that the presence of activated AMPK results in reduced levels of cytoplasmic HuR, and in turn, in reduced concentrations and half-lives of mRNA encoding p21, cyclinA and cyclinB1 (see e.g., *Mol Cell Biol,* 22(10):345-36, 20002, which is incorporated herein by reference). Thus, treatment with contemplated compounds will increase AMPK activity, and thus reduce levels of cytoplasmic HuR, which is though to reduce concentrations/half-lives of a variety of target mRNA transcripts, including those ending p21, cyclinA and cyclinB1.

Premature Apoptosis

Activated AMPK has been shown to provide protection against glucocorticoid-induced apoptosis and to restore cell viability and inhibit DNA laddering in dexamethasone-treated thymocytes (see e.g., Biochem Biophys Res Commun, 243(3):821-6, 1998, which is incorporated herein by reference). Furthermore, activated AMPK has been shown to provide protection against dexamethasone-induced activation of caspase 3-like enzymes, which are believed to play a pivotal role in apoptotic cell death. Thus, treatment with contemplated compounds to increase AMPK activity may provide protection against glucocorticoid-induced apoptosis.

Ischemia

Conditions and disorders associated with AMPK regulation of cellular responses to stresses, including ischemia, are among those treatable by administering a composition comprising a compound that activates AMPK. In several non-vascular tissues, AMPK appears to modulate the cellular response to stresses such as ischemia. In liver and muscle, AMPK phosphorylates and inhibits acetyl CoA carboxylase (ACC), leading to an increase in fatty acid oxidation; in muscle, AMPK activation is associated with an increase in glucose transport. Furthermore, incubation of human umbilical vein endothelial cells (HUVEC) with an AMPK activator has been shown to cause a 5-fold activation of AMPK, which was accompanied by a 70% decrease in ACC activity and a 2-fold increase in fatty acid oxidation. (*Biochem Biophys Res Commun,* 265(1):112-5, 1999, which is incorporated herein by reference). However, in this same study, glucose uptake and glycolysis, the dominant energy-producing pathway in HUVEC, were diminished by 40-60% under these conditions. Despite this, cellular ATP levels were increased by 35%. Thus, treatment with contemplated compounds to increase AMPK activity is expected to result in major alterations in endothelial cell energy balance, which are useful in providing protection against cellular stresses in conditions including ischemia.

Metabolic and Excitotoxic Insults

It is well known in the art that the brain has a high metabolic rate and is relatively sensitive to changes in the supply of glucose and oxygen. The expression of AMPK in embryonic and adult brain and its role in modifying neuronal survival under conditions of cellular stress have been investigated (*J Mol Neurosci,* 17(1): 45-58, 2001). Catalytic (alpha 1 and alpha 2) and noncatalytic (beta 2 and gamma 1) subunits of AMPK are present at high levels in embryonic hippocampal neurons in vivo and in cell culture. In the adult brain, the catalytic subunits alpha 1 and alpha 2 are present in neurons throughout the brain. The AMPK-activating agent AICAR protected hippocampal neurons against death induced by glucose deprivation, chemical hypoxia, and exposure to glutamate and amyloid beta-peptide. Suppression of levels of the AMPK alpha 1 and alpha 2 subunits using antisense technology resulted in enhanced neuronal death following glucose deprivation, and abolished the neuroprotective effect of AICAR. Thus, given the role of AMPK activation in modifying neuronal survival under conditions of cellular stress, treatment with contemplated compounds to increase AMPK activity is thought to provide protection of neurons against metabolic and excitotoxic insults.

Similarly, conditions and disorders associated with hypoxia may be treated using contemplated compounds. AMPK is believed to play a role in regulating ketone body production by astrocytes. (*J Neurochem,* 73(4): 1674-82, 1999). Incubation of astrocytes with AICAR has been shown to stimulate both ketogenesis from palmitate and carnitine palmitoyltransferase I concomitant to a decrease of intracellular malonyl-CoA levels and an inhibition of acetyl-CoA carboxylase/fatty acid synthesis and 3-hydroxy-3-methylglutaryl-CoA reductase/cholesterol synthesis. Moreover, microdialysis experiments have shown AICAR to stimulate brain ketogenesis markedly. Incubation of astrocytes with azide has been shown to lead to a remarkable drop of fatty acid beta-oxidation. However, activation of AMPK during hypoxia was shown to compensate the depression of beta-oxidation, thereby sustaining ketone body production. The effect is believed to rely on the following cascade: hypoxia leads to an increase of the AMP/ATP ratio, which triggers AMPK stimulation, which in turn results in acetyl-CoA carboxylase inhibition. Consequently, malonyl-CoA concentration decreasesm and carnitine palmitoyltransferase I is activated, thus enhancing ketogenesis. Furthermore, incubation of neurons with azide has been shown to blunt lactate oxidation, but not 3-hydroxybutyrate oxidation. Thus, given the role of AMPK activation in regulating ketone body production by astrocytes, treatment with contemplated compounds to increase AMPK activity is useful in promoting astrocytes to produce ketone bodies as a substrate for neuronal oxidative metabolism during hypoxia.

Hepatic Ischemia-Reperfusion

Hepatic ischemia-reperfusion (I/R) injury associated with liver transplantation and hepatic resections may be reduced by administering a composition comprising a compound that activates AMPK. Preconditioning is known to preserve energy metabolism in liver during sustained ischemia. A study has been reported that investigates: 1) whether preconditioning induces AMPK activation; and 2) if AMPK activation leads to ATP preservation and reduced lactate accumulation during prolonged ischemia and its relationship with NO (*Hepatology,* 34(6): 1164-73, 2001). Preconditioning was reported to activate AMPK and concomitantly reduce ATP degradation, lactate accumulation, and hepatic injury. The administration of an AMPK activator, AICAR, before ischemia simulated the benefits of preconditioning on energy metabolism and hepatic injury. The inhibition of AMPK abolished the protective effects of preconditioning. The effect of AMPK on energy metabolism was independent of NO because the inhibition of NO synthesis in the preconditioned group and the administration of the NO donor before ischemia, or to the preconditioned group with previous inhibition of AMPK, had no effect on energy metabolism. Thus, given the role of AMPK activation in the protective effect against ischemia, treatment with contemplated compounds to increase AMPK activity is contemplated for surgical and pharmacological strategies aimed at reducing hepatic I/R injury.

Reduction In Platelet Aggregation

Based on previous findings that kinetin inhibits formation of free radical of activated platelets in vitro and thrombus formation in vivo (Eur. J. Pharmacol. 2003 Apr. 4; 465(3): 281-7, or Platelets. 2003 May; 14(3):189-96), the inventors contemplate that at least some of the compounds presented above may also exhibit platelet aggregation in mammals.

Improvement In Vascular And Cardiovascular Perfusion

Based on previous findings (see e.g., U.S. Pat. Nos. 3,506,643 or 3,502,649) that certain N6-aralkyladenosine derivatives improved vascular and cardiovascular perfusion (thereby increasing oxygenation of associated tissues), the inventors contemplate that at least some of the compounds presented above may also such activity.

Use of Anticytokinins

In another example, numerous diseases and conditions would benefit from a reduction in activation of AMPK in a patient, and the following list provides exemplary guidance on contemplated indications for use of the compounds presented herein.

(1) Recent studies have shown that ventricular tachyarrhythmias frequently arise as a consequence of activated AMPK. Consequently, it is contemplated that compounds according to the inventive subject matter with anti-cytokinins activity may be employed as treatment modalities against ventricular tachyarrhythmias.

(2) It is well established that nutrient deprivation activates AMPK (supra), and that tumors in a relatively early stage are dependent on nutrient diffusion. Thus, when a tumor reaches a critical mass, AMPK will be activated in at least some cells due to lack of glucose and other growth factors. Consequently, the inventors contemplate that contemplated anticytokinins may be employed to block energy salvage pathways of tumor cells (see e.g., Oncogene. 2002 Sep. 5; 21(39):6082-90: Critical roles of AMP-activated protein kinase in constitutive tolerance of cancer cells to nutrient deprivation and tumor formation by Kato et al.).

Therefore, it should be appreciated that contemplated pharmaceutical compositions and contemplated compounds may especially beneficial to a person to (1) reduce fatty acid synthesis, sterol synthesis, triglyceride synthesis and fatty acid synthase gene expression, (2) ameliorate one or more conditions or disorders that are characterized by elevations in one or more of the pathways or mechanisms involved in fatty acid synthesis, sterol synthesis, triglyceride synthesis and fatty acid synthase gene expression, (3) increase fatty acid oxidation and ketogenesis, (4) inhibit lipogenesis and/or isoprenaline-stimulated lipolysis, (5) ameliorate one or more conditions or disorders that are characterized by elevations in one or both of lipogenesis and isoprenaline-stimulated lipolysis pathways, or that are exacerbated by the elevations in one or both of these pathways, (6) decrease insulin secretion, (7) ameliorate one or more a conditions or disorders that are characterized by elevated insulin secretion, or that are exacerbated by insulin secretion, (8) enhance glucose uptake in muscle cells, (9) ameliorate one or more conditions or disorders that are characterized by decreased glucose uptake in muscle cells, or that are exacerbated by the effects of decreased glucose uptake in muscle cells, (10) inhibit adipogenesis, (11) ameliorate one or more conditions or disorders that are characterized by increased adipogenesis, or that are exacerbated by adipogenesis, (12) increase insulin sensitivity of muscle glucose transport, (13) lower blood glucose concentrations by decreasing hepatic glucose production and/or increasing glucose disposal in skeletal muscle, and/or (14) ameliorate one or more conditions or disorders associated with insulin resistance syndrome through improving glucose tolerance, improving lipid profile or reducing systolic blood pressure.

It should be especially appreciated that traditional long term metformin therapy often requires concurrent supplementation with calcium carbonate to prevent the adverse impact of metformin administration on vitamin B12 absorption. It has been postulated that the hydrophobic tail of biguanides, such as metformin, extends into the hydrophobic core of membranes, thereby adding a positive charge to the surface of the membrane, which acts to displace divalent cations (see e.g., Bauman et al. (Diabetes Care 2000; 23:1227-31)), which in turn negatively affects binding of the B12-intrinsic factor complex to the ileal cell surface receptors. Such adverse consequences are not expected using most of the contemplated compounds as they are significantly structurally different from biguanides.

Consequently, the inventors contemplate a method of modulating glucose metabolism in a mammal in which in one step a contemplated compound/pharmaceutical composition is administered to a the mammal at a dosage effective to modulate glucose metabolism in the mammal. In especially contemplated aspects, the mammal is a human and diagnosed with syndrome X, pre-diabetes, insulin resistance, type-2 diabetes, and/or dyslipidemia. Additionally, or alternatively, contemplated compounds/pharmaceutical compositions may also be prophylactically administered to prevent or delay onset or progression of syndrome X, pre-diabetes, insulin resistance, type-2 diabetes, and/or dyslipidemia. While not limiting to the inventive subject matter, the inventors contemplate that such treatment may be due to an increase in glucose uptake into a muscle cell (or other cell), and/or due to a decrease in gluconeogenesis in a hepatocyte. With respect to the hepatocyte, and while not limiting to the inventive subject matter, the inventors contemplate that the compounds presented herein will directly or indirectly affect activity of the glucocorticoid receptor, PEPCK (phosphoenolpyruvate carboxykinase), the glucagon receptor, and/or glucose-6-phosphatase.

Similarly, in further preferred aspects, the inventors contemplate a method of modulating lipid metabolism in a mammal in which in one step a contemplated compound/pharmaceutical composition is administered to a the mammal at a dosage effective to modulate glucose metabolism in the mammal (wherein the compound preferably is not an N6-aralkyladenosine). Such methods may advantageously be employed to treat or prevent syndrome X and/or dyslipidemia, and may also be employed to decrease at least one of total serum cholesterol, serum LDL-cholesterol, and serum triglycerides.

Viewed from another perspective, the inventors also contemplate a method of treating a condition in a mammal, wherein the condition is associated with a dysregulation of at least one of AMPK and Akt (e.g., over-expression or under-expression of AMPK and/or Akt as compared to normal cells, or over-activation or under-activation of AMPK and/or Akt as compared to normal cells). In such methods, a contemplated compound/pharmaceutical composition is administered to the mammal at a dosage effective to activate at least one of AMPK and Akt. Where anti-cytokinins are employed, the contemplated compound/pharmaceutical composition is administered to the mammal at a dosage effective to reduce activation at least one of AMPK and Akt. Among other conditions, especially contemplated conditions for such methods include cardiovascular disease, type 2 diabetes, and a neoplastic disease.

EXPERIMENTS

In Vitro Effect of Selected Compounds on Glut-4, activated AMPK, and activated Akt The levels of Glut-4, activated AMPK and activated Akt were measured in mouse muscle cells C2C12 (from ATTC) and in primary culture of human skeletal muscle cells (Clonetics, Inc.) using Western immunoblotting. C2C12 cells were plated at 1.5×1–exp5 cells per mL/well (12-well plate) in standard cell culture medium (DMEM supplemented with 10% fetal bovine serum (FBS), 25 mM glucose, 20 mM Hepes, 4 mM glutamine and 2 mM sodium pyruvate. 48 hrs after the plating, medium was changed to differentiation medium (DMEM supplemented with 5 mM of glucose and 0.5% of FBS) for next 3-4 days to stimulate the formation of myotubes. Three hrs before the treatment with selected agents, cells were washed with PBS and transferred to PBS supplemented with 5 mM of glucose.

Human skeletal muscle cells (HSKM) were cultured in SKBM-2 mediums provided by Clonetics. 48 hrs after cell plating, medium was changed to SKBM medium to stimulate differentiation of the cells to myotubes. When differentiated, the myotubes were transferred to PBS supplemented with 5 mM glucose for three hrs before the treatment.

Analysis of C2C12 cells for the level of activated AMPK, Akt and the level of GLUT-4 was performed in the same experimental system. The cells were treated for 30 minutes at 37° C. After the treatment, the cells were washed with ice-cold PBS and lysed with 80 µl of lysis buffer/well (M-PER buffer from Pierce supplemented with protease and phosphatase inhibitor mix (Calbiochem) for 10 minutes on ice. Next, the plates were transferred to −20° C. to improve the lysis of the cells. Next cells were sonicated for 5 minutes and lysate was transferred to Eppendorf tubes and centrifuged at 14,000 rpm for 10 minutes. Supernatants were collected in fresh Eppendorf tubes and kept on ice to measure the amount of total proteins. 3 µl of each lysate was used to measure the protein concentration using standard Bradford method (Biorad). Subsequently, 20 µg per sample of sample protein was used for Western analysis using NuPage 10% Bis/Tris gels (Invitrogen). After exposure of membranes to primary and secondary antibodies AMPK, AKT or Glut-4 was detected using ECL-Plus (Amersham) following producer's instruction. Chemilumiscent signals were detected by using Chemi-Doc system from Biorad. Intensity of detected signals were analyzed and measured using Quantity One software (Biorad). Alternatively, the level of phosphorylated AMPK was detected using ECL kit from Amersham and short exposure to Kodak films.

Experimental setup: Cell Culture was followed by treatment with selected contemplated compounds, which was followed by cell lysis and western blot analysis for AMPK, Akt, GLUT4, total AMPK, and total Akt. Signals were acquired accordingly. Primary antibodies used in these studies are the following: Anti-phospho-AMPK (Thr172), mouse, rabbit IgG, from Cell Signaling, #2531; Anti-phospho-Akt (Ser473), mouse, rabbit IgG, Cell Signaling, #9271; Anti-Glut-4, mouse, rabbit IgG, Calbiochem, #400064; Anti-AMPK (total), mouse, rabbit IgG, Cell Signaling, #2532; Anti-Akt (total), mouse, rabbit IgG, Cell Signaling, #9272.

(1) Results for AMPK Activation

The effects of various compounds (some data not shown) on AMPK activity are summarized in Table 1 below. The results demonstrate that most of the tested agents significantly stimulate AMPK activity, with some resulting in over 10 fold increases in activity compared the untreated control. The more potent compounds include derivatives of adenine, cytidine and guanosine as well as kinetin and zeatin. Table 1 refers to multiple independent experiments where multiple identical concentrations for the same reagents are indicated.

TABLE 1

| AGENT | CONCENTRATION (microM) | FOLD AMPK ACTIVATION (OVER CONTROL) |
|---|---|---|
| Adenosine | 12.5 | 1.83 |
|  | 5.0 | 1.64 |
|  | 2.5 | 1.87 |
| $N^6$-Acetyl-Adenosine | 12.5 | 2.18 |
|  | 5.0 | 2.41 |
|  | 2.5 | 1.08 |
| Benzyl-Adenine | 50.0 | 2.92 |
|  | 5.0 | 2.70 |
|  | 0.5 | 2.18 |
| Gamma, Gamma-Dimethylally-6-Aminopurine | 50.0 | 2.11 |
|  | 5.0 | 2.45 |
|  | 0.5 | 2.82 |
| Dihydro-Zeatin | 50.0 | 0.88 |
|  | 5.0 | 0.59 |
|  | 0.5 | 2.25 |
| Zeatin | 1.0 | 2.33 |
|  | 10.0 | 2.04 |
|  | 1.0 | 2.15 |
| Trans-Zeatin | 10.0 | 4.27 |
|  | 1.0 | 2.33 |
| Guanosine | 5.0 | 3.70 |
| $N^2$-Acetyl-Guanosine | 2.0 | 2.20 |
|  | 0.8 | 2.20 |
|  | 0.3 | 3.75 |
|  | 1.5 | 4.28 |
|  | 7.5 | 1.71 |
|  | 37.5 | 2.28 |
| $N^2$-Acetyl-Guanine | 0.3 | 5.42 |
|  | 1.5 | 5.85 |
|  | 7.5 | 6.00 |
|  | 37.5 | 6.51 |
| Kinetin | 0.8 | 3.60 |
|  | 0.8 | 2.40 |
|  | 2.0 | 2.70 |
|  | 10.0 | 12.80 |
|  | 0.1 | 5.30 |
|  | 0.3 | 8.12 |
|  | 1.0 | 19.50 |
|  | 3.0 | 14.50 |
| Kinetin Riboside | 3.0 | 12.00 |
| Metformin | 2.0 milliM | 1.42 |
| Rosiglitazone | 3.0 | 3.50 |

(2) Results for Akt Activity

The effects of selected compounds on Akt activity are summarized in Table 2 below. Interestingly, many of the potent AMPK stimulators had only marginal effect on Akt activity. For example, zeatin is a potent stimulator of AMPK but not Akt. However, guanosine, $N^2$-Acetyl-Guanosine and $N^2$-Acetyl-Guanine were observed to be potent activators of AMPK as well as Akt. Table 2 refers to multiple independent experiments where multiple identical concentrations for the same reagents are indicated.

TABLE 2

| AGENT | CONCENTRATION (microM) | FOLD AKT ACTIVATION (OVER CONTROL) |
|---|---|---|
| Kinetin | 5.0 | 2.07 |
| | 2.0 | 3.35 |
| | 0.8 | 3.17 |
| | 8.1 | 0.24 |
| | 2.7 | 3.21 |
| | 0.9 | 3.81 |
| | 0.3 | 5.08 |
| Kinetin Riboside | 5.0 | 3.32 |
| | 2.0 | 5.14 |
| | 0.8 | 3.71 |
| Zeatin | 10.0 | 1.36 |
| | 1.0 | 0.95 |
| Trans-Zeatin | 10.0 | 0.86 |
| | 1.0 | 0.90 |
| Gamma, Gamma-Dimethylally-6-Aminopurine | 2.0 | 1.32 |
| | 0.8 | 1.90 |
| | 0.8 | 3.56 |
| $N^4$-Acetyl-Cytidine | 5.0 | 1.64 |
| | 2.0 | 1.46 |
| | 0.8 | 2.45 |
| | 5.0 | 1.36 |
| | 2.0 | 1.50 |
| $N^2$-Acetyl-Guanosine | 5.0 | 1.23 |
| | 0.8 | 1.75 |
| | 0.3 | 1.92 |
| | 0.1 | 2.57 |
| | 2.0 | 2.17 |
| | 0.8 | 2.95 |
| | 7.5 | 1.68 |
| | 1.5 | 1.55 |
| | 0.3 | 2.57 |
| $N^2$-Acetyl-Guanine | 7.5 | 2.58 |
| | 1.5 | 3.58 |
| | 0.3 | 3.50 |
| | 7.5 | 1.95 |
| | 1.5 | 1.64 |
| | 0.3 | 2.44 |
| AICAR | 500.0 | 5.45 |
| | 50.0 | 2.20 |
| Metformin | 20.0 milliM | 2.32 |
| | 2.0 milliM | 2.70 |
| Insulin | 0.10 nanoM | 1.75 |
| | 50.0 nanoM | 3.28 |
| | 25.0 nanoM | 3.40 |
| Rosiglitazone | 27.0 | 0.71 |
| | 9.0 | 1.78 |
| | 3.0 | 2.34 |
| | 3.0 | 5.01 |
| | 1.0 | 2.83 |

(3) Results for GLUT-4

The effects of kinetin, $N^2$-Acetyl-Guanosine and $N^2$-Acetyl-Guanine on GLUT-4 protein level in C2C12 cells were investigated following the same experimental design as described for AMPK and AKT. Anti-Glut-4 antibody used in this study was from Calbiochem. The results summarized in Table 3 below demonstrate that kinetin, $N^2$-Acetyl-Guanosine and $N^2$-Acetyl-Guanine potently increase GLUT-4 protein level in C2C12 cells at different range and in a dose-dependent manner. Table 3 refers to multiple independent experiments where multiple identical concentrations for the same reagents are indicated.

TABLE 3

| AGENT | CONCENTRATION (microM) | FOLD CHANGE IN GLUT-4 LEVEL (OVER CONTROL) |
|---|---|---|
| Rosiglitazone | 3.0 | 3.82 |
| | 9.0 | 3.61 |
| | 27.0 | 3.19 |
| | 3.0 | 2.13 |
| | 3.0 | 4.37 |
| | 3.0 | 2.98 |
| Metformin | 2000 | 1.50 |
| Kinetin | 0.3 | 3.45 |
| | 0.9 | 4.00 |
| | 2.7 | 3.88 |
| | 8.1 | 1.11 |
| | 0.8 | 3.46 |
| | 0.3 | 3.95 |
| | 0.8 | 2.36 |
| | 2.0 | 1.88 |
| $N^2$-Acetyl-Guanine | 0.3 | 3.94 |
| | 1.5 | 3.84 |
| | 7.5 | 3.24 |
| | 37.5 | 2.80 |
| $N^2$-Acetyl-Guanosine | 0.3 | 1.21 |
| | 1.5 | 1.74 |
| | 7.5 | 3.14 |
| | 37.5 | 3.03 |

In Vitro Myocyte Glucose Uptake

Total glucose uptake was measured using fluorescent glucose analog from Molecular Probes. Briefly, muscle cells were treated with kinetin, $N^2$-Acetyl-Guanosine and $N^2$-Acetyl-Guanine for 30 minutes at 37 C first and subsequently, these cells were exposed to 500 μM of fluorescent glucose analog for 5 minutes at room temperature. Next, cells were washed twice with cold Krebs-Hepes buffered solution and fixed in 70% ethanol in water. Fluorescence of fluorescent glucose in the cells was measured using fluorescent plate reader at 480/530 nm (excitation/emission). The results summarized in Table 4 below demonstrate that kinetin, $N^2$-Acetyl-Guanosine and $N^2$-Acetyl-Guanine each potently enhance glucose uptake in muscle cells in vitro. Table 4 refers to multiple independent experiments where multiple identical concentrations for the same reagents are indicated.

TABLE 4

| AGENT | CONCENTRATION (microM) | AVERAGE (N = 3) | FOLD CHANGE IN TOTAL GLUCOSE UPTAKE (OVER CONTROL) |
|---|---|---|---|
| $N^2$-Acetyl-Guanosine | 0.0 | 20.3 +/- 0.1 | — |
| | 0.3 | 44.1 +/- 0.7 | 2.17 |
| | 1.5 | 54.3 +/- 0.9 | 2.67 |
| | 7.5 | 61.7 +/- 1.3 | 3.03 |
| | 0.00 | 46.5 +/- 1.2 | — |
| | 0.15 | 90.5 +/- 1.7 | 1.94 |
| | 0.75 | 109.5 +/- 2.6 | 2.35 |
| | 3.75 | 148.7 +/- 8.5 | 3.18 |
| $N^2$-Acetyl-Guanine | 0.3 | 54.5 +/- 1.7 | 2.68 |
| | 1.5 | 55.2 +/- 0.8 | 2.71 |
| | 7.5 | 59.6 +/- 0.4 | 2.93 |
| | 0.00 | 46.5 +/- 1.2 | — |
| | 0.15 | 86.4 +/- 2.3 | 1.85 |
| | 3.75 | 115.9 +/- 3.7 | 2.48 |

TABLE 4-continued

| AGENT | CONCEN-TRATION (microM) | AVERAGE (N = 3) | FOLD CHANGE IN TOTAL GLUCOSE UPTAKE (OVER CONTROL) |
|---|---|---|---|
| Kinetin | 0.00 | 47 +/− 0.7 | — |
| | 0.15 | 88.6 +/− 0.9 | 1.88 |
| | 0.75 | 103.3 +/− 2.1 | 2.19 |
| | 3.75 | 102.6 +/− 4.7 | 2.18 |
| | 0.0 | 28.9 +/− 0.1 | — |
| | 0.3 | 86.0 +/− 0.7 | 2.97 |
| | 1.5 | 110.6 +/− 2.3 | 3.82 |
| | 7.5 | 56.6 +/− 1.4 | 1.95 |
| Rosiglitazone | 3.0 | 47.3 +/− 1.1 | 2.33 |
| | 30.0 | 56.5 +/− 1.4 | 2.78 |
| | 0.0 | 52.1 +/− 0.2 | — |
| | 3.0 | 122.4 +/− 3.7 | 2.34 |

Ex Vivo Glucose Uptake in Rat Epitrochlearis Muscle

Glucose uptake in rat epitrochlearis muscle was determined following a protocol substantially as described by Brozinick, J. T., and Birnbaum, M. J. (1998) J. Biol. Chem. 273(24), 14679-146822. Results are listed in Tables 5 and 6, wherein data of Table 5 were obtained for 60 minute incubations and data of Table 6 were obtained for 120 minute incubations of the compounds as indicated (K is kinetin, AG is N2-acetylguanine).

TABLE 5

| | DATA | | | |
|---|---|---|---|---|
| | CONTROL Basal | K 0.5 uM | K 2 uM | AG 0.1 uM | AG 0.4 uM |
| Raw | 0.55 | 0.82 | 0.57 | 0.66 | 0.63 |
| Raw | 0.48 | 0.88 | 0.90 | 1.85 | 2.28 |
| Raw | 1.23 | 1.47 | 0.64 | 0.86 | 1.61 |
| Raw | 0.69 | 0.56 | 0.81 | 0.87 | 1.35 |
| Raw | 1.35 | 1.19 | 0.57 | 1.35 | 1.27 |
| Mean | 0.82 | 0.99 | 0.70 | 1.12 | 1.43 |
| StDev | 0.38 | 0.35 | 0.15 | 0.48 | 0.60 |
| Sem | 0.15 | 0.16 | 0.07 | 0.22 | 0.27 |

TABLE 6

| | DATA | |
|---|---|---|
| Media | CONTROL Basal | K 1 uM |
| Raw | 1.06 | 1.54 |
| Raw | 0.97 | 0.95 |
| Raw | 0.72 | 1.33 |
| Raw | 1.15 | 1.10 |
| Raw | 0.78 | 1.23 |
| Mean | 0.94 | 1.23 |
| Stdev | 0.18 | 0.23 |
| Sem | 0.08 | 0.10 |

Effect of Cytokinin-Enriched Preparations on Serum Glucose and Lipids In Vitro Two separate cytokinin-containing extracts (PE1, PE2) were prepared from sprouted barley according to a protocol similar to the protocols presented in WO2004/021980, WO01/66146, or WO02/072148, each of which are incorporated by reference herein. PE1 and PE2 were confirmed by HPLC and LC/MS to include among other compounds kinetin and dihydrozeatin. Uptake of 1-deoxy-D-[3H]glucose in primary culture of rat adipocytes was measured in presence of a combination of PE1 and PE2, insulin, and a combination PE1/PE2 and insulin. Table 7 depicts the results of this experiment in which the effect is listed as % increase of control at various concentrations for PE1/PE2.

TABLE 7

| | PE1/PE2 | PE1/PE2 + INSULIN |
|---|---|---|
| 0.05 mg/ml | 100 | 225 |
| 0.1 mg/ml | 155 | 270 |
| 1.0 mg/ml | 155 | 360 |
| 1.2 mg/ml | 150 | 340 |

Similar results were obtained in L6 muscle cells (without insulin), wherein doses of 50 microgram/ml stimulated glucose uptake over 65% as compared to control.

Effect of Cytokinin-Enriched Preparations on Serum Glucose and Lipids in Rats

The above cytokinin-enriched preparations (PE1/PE2) were further administered to streptozocin treated rats, and the results were compared with streptozocin treated rats that received metformin as control. Administration of PE1/PE2 was at 85 mg/kg, whereas metformin was administered at 500 mg/kg. Remarkably, rats treated with PE1/PE2 showed reduced blood glucose levels comparable to Metformin, while PE1/PE2 greatly improved liver enzymes over streptozocin group and equivalent to Metformin. Furthermore, PE1/PE2 prevented body weight loss more effectively than Metformin.

Effect of Cytokinin-Enriched Preparations on Serum Glucose and Lipids in Human

The above cytokinin-enriched preparations (PE1/PE2) were also orally administered to ten patients diagnosed with type 2 diabetes over a period of ninety days. The total daily dose was 7.5 gram (3×2.5 g) per patient, and blood analyses were performed at day 0, 45 and 90 day. Most significantly, the results unequivocally revealed a 20% decrease in fasting and postprandial serum glucose, significant improvement of glucose tolerance, 14% decrease in glycosylated hemoglobin, and a 20% decrease in LDL/HDL ratio.

Oral Availability and Serum Determination of Selected Cytokinins

C57/B1 mice were treated with 100 microgram/dose of dihydrozeatin (DHZ) for 0, 15, 30, 60 and 120 minutes following oral or i.p. administration. Serum level of DHZ in pg/ml was measured using DHZ Elisa following procedures as enclosed in a commercially available test kit (e.g., dihydrozeatin competitive ELISA test system for plant growth hormone detection, Agdia, Elkhard, Ind.). Three animals were used per experimental point.

TABLE 7

| | TIME | | | | |
|---|---|---|---|---|---|
| ROUTE | 0 | 15 | 30 | 60 | 120 |
| Oral | 300 | 952 | 1024 | 961 | 853 |
| i.p. | 300 | 1154 | 991 | 746 | 471 |

As can be clearly taken from the data, DHZ is readily bioavailable from the oral route and significant serum concentrations can be maintained over at least 120 minutes. Even more remarkably, at time point 0 minutes, the inventors discovered a significant DHZ concentration in serum, which suggests that if DHZ or other cytokinins as contemplated above is implicated in metabolic modulation (of glucose and/or lipid metabolism) and present in serum, various metabolic conditions and/or diseases may be monitored by determination of DHZ or other cytokinins. Consequently, the inventors contemplate a method of performing an analytic test in a mammal (preferably human) comprising one step in which the concentration of one or more of contemplated compounds is determined in a biological fluid. In a further step of such method, the concentration is correlated with a likelihood and/or presence of a metabolic disorder (e.g., pre-diabetes, insulin resistance, type-2 diabetes, syndrome X, dyslipidemia, or any condition that is associated with dysfunction of AMPK and/or Akt). Typically, it is expected that a decrease in the concentration of the compound in the biological fluid will be associated with the likelihood and/or presence of the metabolic disorder.

Furthermore, it is contemplated that one or more of the compounds presented herein may be a factor in a mammal that is implicated in metabolic control and therefore present at a certain serum and/or cellular concentration. In such case, depletion or one or more of such factors may lead to a metabolic disturbance, which may present a disease or condition, including pre-diabetes, insulin resistance, type-2 diabetes, syndrome X, and/or dyslipidemia. Therefore, contemplated pharmaceutical compositions may also be advertised and/or ingested to normalize and/or enhance the cellular and/or serum concentration of the compound with cytokinin activity.

Thus, specific embodiments and applications of pharmaceutical compositions and methods for metabolic modulation have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A method of activating AMPK to thereby increase glucose uptake into a cell and thereby treat a condition selected from the group consisting of syndrome X, pre-diabetes, insulin resistance, and type 2 diabetes, the method comprising:
    providing an isolated or synthetic cytokinin in combination with a pharmaceutically or nutritionally acceptable carrier to a patient at a dosage effective to activate the AMPK in the cell; and
    wherein the cytokinin is selected from the group consisting of $N^6$-acetyl-adenosine, benzyl-adenine, gamma, gamma-dimethylally-6-aminopurine, dihydro-zeatin, zeatin, trans-zeatin, $N^2$-acetyl-guanosine, $N^2$-acetyl-guanine, kinetin, and kinetin riboside.

2. The method of claim 1 wherein the dosage is further effective to activate Akt in the cell.

3. The method of claim 1 wherein the dosage is further effective to increase glucose uptake into a muscle or to increase GLUT-4 levels in the cell.

4. The method of claim 1 wherein the dosage is effective to decrease serum glucose in the patient.

5. The method of claim 4 wherein the dosage is also effective to decrease a serum lipid in the patient.

6. A method of treatment of a condition selected from the group consisting of syndrome X, pre-diabetes, insulin resistance, and type 2 diabetes, the method comprising:
    administering to a patient an isolated or synthetic cytokinin and a pharmaceutically or nutritionally acceptable carrier to the patient at a dosage effective to treat the condition;
    wherein the cytokinin is selected from the group consisting of $N^6$-acetyl-adenosine, benzyl-adenine, gamma, gamma-dimethylally-6-aminopurine, dihydro-zeatin, zeatin, trans-zeatin, $N^2$-acetyl-guanosine, $N^2$-acetyl-guanine, kinetin, and kinetin riboside.

7. The method of claim 6 wherein the cytokinin is dihydro-zeatin, zeatin, or trans-zeatin.

8. The method of claim 6 wherein the cytokinin is kinetin or kinetin riboside.

9. The method of claim 6 wherein the cytokinin is $N^6$-acetyl-adenosine, benzyl-adenine, $N^2$-acetyl-guanosine, or $N^2$-acetyl-guanine.

10. The method of claim 6 wherein the cytokinin is administered in form of a nutritional supplement.

11. The method of claim 6 wherein the dosage is effective to activate AMPK in a cell of the patient.

12. The method of claim 6 wherein the dosage is effective to activate Akt in a cell of the patient.

13. The method of claim 6 wherein the dosage is effective to increase GLUT-4 in a cell of the patient.

14. The method of claim 6 wherein the dosage is effective to decrease serum glucose and optionally serum lipids in the patient.

* * * * *